US006558704B1

(12) United States Patent
Bartholomaeus et al.

(10) Patent No.: US 6,558,704 B1
(45) Date of Patent: May 6, 2003

(54) PROCESS FOR PREPARING PELLETS CONTAINING UP TO 90 WT.% OF A PHARMACEUTICAL ACTIVE INGREDIENT

(75) Inventors: Johannes Heinrich Bartholomaeus, Aachen (DE); Iris Ziegler, Rott-Roetgen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 09/484,015

(22) Filed: Jan. 18, 2000

(30) Foreign Application Priority Data

Jan. 18, 1999 (DE) .......................................... 199 01 692

(51) Int. Cl.$^7$ ............................. A61K 9/14; A61K 9/50; A61K 9/20; A61K 9/48
(52) U.S. Cl. ....................... 424/489; 424/489; 424/490; 424/499; 424/502; 424/464; 424/451
(58) Field of Search ................................. 424/489, 490, 424/464, 451, 499, 502

(56) References Cited

U.S. PATENT DOCUMENTS 5,352,460 A    10/1994   Sipos

OTHER PUBLICATIONS

Hileman et al., "A Factorial Approach to High Dose Product Development by an Extrusion/Spheronization Process", *Drug Development and Industrial Pharmacy*, 19(4), pp. 483–491.
Jover et al., "Evaluation, by a Stastically Designed Experiment, of an Experimental Grade of Microcrystalline Cellulose, Avicel 955, as a Technology to Aid the Production of Pellets with High Drug Loading", *Journal of Pharmaceutical Sciences*, vol. 85, No. 7, Jul. 7, 1996, pp. 700–705.
Bains et al., "The Influence of Moisture Content on the Preparation of Spherical Granules of Barium Sulphate and Microcrystalline Cellulose", Nov. 7, 1990.
Lundqvist et al., "Influence of Disintegrant Type and Proportion on the Properties of Tablets Produced from Mixtures of Pellets", *International Journal of Pharmaceutics*, Nov. 7, 1996, pp. 95–107.
Hileman et al., "Response Surface Optimization of High Dose Pellets by Extrusion and Spheronization", *International Journal of Pharmaceutics*, Apr. 22, 1993, pp. 71–79.
Dressman et al., Storage Effects on Release from Phenylpropanolamine HCl Pellets Coated with an Ethylcellulose--based film, Proceedings of the 18$^{th}$ International Symposium on Controlled Release of Bioactive Materials, Jul. 8–11, 1991, pp. 654–655.
Kleinebudde, "The Crystallite–Gel–Model for Microcrystalline Cellulose in Wet–Granulation, Extrusion, and Spheronization", *Pharmaceutical Research*, vol. 14, No. 6, 1997, pp. 804–809.
Lustig et al., "The Influence of the Properties of Drug on the Preparation of Spherical Pellets by Extrusion/Spheronization", *1$^{st}$ World Meeting on Pharmaceutics, Biopharmaceutics and Pharmaceutical Technology*, May 9–11, 1995, pp. 349–350.
Kleinebudde, "Shrinking and Swelling Properties of Pellets Containing Microcrystalline Cellulose and Low Substituted Hydroxypropylcellulose: I. Shrinking Properties", *International Journal of Pharmaceutics*, Feb. 28, 1994, pp. 209–219.
Newton, "The Preparation of Spherical Granules by Extrusion/Spheronisation", *Sciences Pharmacéutiques Revue*, 1990, pp. 396–398.
Schmidt et al., "Comparison Between a Twin–Screw Extruder and a Rotary Ring Die Press. I. Influence of Formulation Variables", *European Journal of Pharmaceutics and Biopharmaceutics*, May 30, 1997, pp. 169–176.
Newton et al., "The Effect of Excipient Source of Spherical Granules Made by Extrusion/Spheronization", *Pharmaceutical Technology International*, Oct. 1992, pp. 52–58.
Hileman et al., "Drug Solubility Effects on Predicting Optimum Conditions for Extrusion and Spheronization of Pellets", *Pharmaceutical Development and Technology*, 1977, pp. 43–52.
O'Connor et al., "Spheronization II: Drug Release from Drug–Diluent Mixtures", *Drug Development and Industrial Pharmacy*, 1985, pp. 1837–1857.
Bianchini et al., "Oral Controlled Release Optimization of Pellets Prepared by Extrusion–Spheronization Processing", *Il Farmaco*, 1989, pp. 645–654.
Follonier et al., "Evaluation of Hot–Melt Extrusion as a New Technique for the Production of Polymer–Based Pellets for Sustained Release Capsules Containing High Loadings of Freely Soluble Drugs", *Drug Development and Industrial Pharmacy*, 1994, pp. 1323–1339.
Vervaet et al., "Influence of Impeller Design, Method of Screen Perforation and Perforation Geometry on the Quality of Pellets Made by Extrusion–Spheronization", *International Journal of Pharmaceutics*, 1996, pp. 29–37.

(List continued on next page.)

Primary Examiner—Thurman K. Page
Assistant Examiner—Amy E Pulliam
(74) Attorney, Agent, or Firm—Crowell & Moring LLP

(57) ABSTRACT

A process for the preparation of pellets containing $\geq 50$ wt. % of a pharmaceutical active ingredient having a solubility in water of $\geq 0.5$ g/ml, by aqueous granulation of the mixture containing the active ingredient, extrusion, rounding and drying of the moist granules, using a mixture consisting of A) at least 50 wt. % of at least one active ingredient having a solubility in water of $\geq 0.5$ g/ml, and
B) at most 50 wt. % of the combination of
  a) a microcrystalline cellulose having an average particle size of 15 to 20 $\mu$m and
  b) a low-substituted hydropropyl cellulose having an average particle size in the range of 10 to 25 $\mu$m, the weight ratio of a):b) being in the range of 4:6 to 6:4.

11 Claims, No Drawings

OTHER PUBLICATIONS

Širca et al., "Formulation and Process Development of Extrusion/Spheronization Pellets", The Second Central European Symposium on Pharmaceutical Technology, 1997, pp. 310–311.

Thoma et al., "Investigations on the Influence of the Type of Extruder for Pelletization by Extrusion–Spheronization. I. Extrusion Behavior of Formulations", *Drug Dev. Ind. Pharm.* 1998, pp. 401–411 (abstract only).

Onodera et al., "Production of Pellet Feeds for Cattle Prepared from Shochu Distiller's Byproduct by Extruder", *Miyazaki Daigaku Nogakubu Kenkyu Hokoku*, 1997, pp. 45–53 (abstract only).

Chatlapalli et al., "Physical Characterization of HPMC and HEC and Investigation of Their Use as Pelletization Aids", *Int. J. Pharm*, 1998, pp. 179–193 (abstract only).

Follonier et al., "Various Ways of Modulating the Release of Diltiazem Hydrochloride from Hot–Melt Extruded Sustained–Release Pellets Prepared Using Polymeric Materials", *J. Controlled Release*, 1995, pp. 243–250 (abstract only).

Venkatesh et al., "Controlled Drug Delivery of pH–dependent Soluble Drug, Pindolol", *Drug Dev. Ind. Pharm.*, 1994, pp. 111–118 (abstract only).

Baert et al., "Comparison Between a Gravity Feed Extruder and a Twin Screw Extruder", *Int. J. Pharm.*, 1993, pp. 7–12 (abstract only).

Follonier et al., "Hot–Melt Extruded Pellets for the Sustained Release of Highly Dosed Freely Soluble Drugs", Proceedings Program, Int. Symp. Controlled Release Bioactive Materials, $18^{th}$, 1991, pp. 578–579 (abstract only).

Knop et al., "Manufacture of Granules and Pellets in a Pneumatically Rotating Fluidized Bed", *Pharm. Acta Helv.*, 1992, pp. 104–112 (abstract only).

Bianchini et al., "Influence of Extrusion–Spheronization Processing on the Physical Properties of d–indobufen Pellets Containing pH Adjusters", *Drug Dev. Ind. Pharm.*, 1992, pp. 1485–1503 (abstract only).

Tez, "Production and Properties of Extgruded Porous Molded Bodies from Aluminum Oxide", Marmara Univ. Fen Bilimleri Derg., 1989, pp. 227–244 (abstract only).

Onofrei, "Sol–Gel Extrusion Process for Fabrication of Thorium Dioxide–Uranium Dioxide Recycle Fuel", *J. Nucl. Mater*, 1986, pp. 207–211 (abstract only).

Stoops, "Liquid Phase Extrusion Hot–Pressing", *Amer. Ceram. Soc., Bull.*, 1969, pp. 225–227 (abstract only).

Fitts et al., "Preparation of Ceramic Nuclear Fuels by Sol–Gel Extrusion", Chem. Eng. Prog., Symp. Ser. 1967, pp. 28–33 (abstract only).

Remington's Pharmaceutical Sciences. 18 edition, 1990, pp 1635–1636.*

* cited by examiner

PROCESS FOR PREPARING PELLETS CONTAINING UP TO 90 WT.% OF A PHARMACEUTICAL ACTIVE INGREDIENT

BACKGROUND OF THE INVENTION

The present invention relates to a process for the preparation of pellets with a content of up to 90 wt. % of a pharmaceutical active ingredient having an extremely high solubility in water, by aqueous moist extrusion and subsequent spheronization.

Extrusion and subsequent spheronization is a long-known method for the preparation of granules having a defined shape and particle size which has also gained great importance in the production of pharmaceutical pellets (J. W. Conine et al., Drug & Cosmetic Ind. 106, 38–41 (1970)). At the same time the processing of numerous pharmaceutical active ingredients has also been described. Such multiparticulate forms of administration are often preferred to monolithic dosage forms due to improved bioavailability, pharmaceutical safety and reliability of action. Moreover, there exists a comprehensive body of literature dealing with optimizing the conditions of preparation, with the effect of the composition of the formulation and with the differences between various types of extruder as well as with the principles of extrusion/spheronization (L. Hellen et al., Int. J. Pharm., 95, 197–204 and 205–216 (1993); L. Baert et al., Int. J. Pharm., 96, 225–229 (1993) and Int. J. Pharm., 81, 225–223 (1992) and Int. J. Pharm., 97, 79–92 (1993); K. Thoma et al., Drug Dev. Ind. Pharm., 24 (5), 401–411 (1998)).

The advantages of extrusion/spheronization over pelletizing in the preparation of pellets include, among other factors, a greater compression of the pellets. Because of this, homogeneous pellets having a high content of active ingredients, that is, a content of active ingredients of up to 90 wt. %, can be obtained by the aforementioned method. Moreover, the pellets prepared by extrusion/spheronization are not only denser, but the surface of the pellets also has a lower porosity, so that the amount of functional films applied to the pellets can be distinctly decreased and more even release profiles can be achieved (G. Zhang et al., Drug Dev. Ind. Pharm., 16 (7), 1171–1184 (1990)). For this reason the preferred method for the preparation of pellets, in particular for the preparation of high-dosage pellets which are provided with coatings having a controlled-release action, is by extrusion/spheronization.

Besides the so-called melt extrusion, extrusion of granules moistened with water is one of the most common extrusion methods. In this process the active ingredients together with the auxiliary substances are granulated with the addition of water and then extruded, after which the extrudates are rounded in a spheroniser and dried. This method has the advantage over melt extrusion that it avoids undesirable heat load on the mixtures containing the active ingredients.

While pellets having a high content of active ingredients of up to 90 wt. %, even for active ingredients with a good to very good solubility in water, can be prepared by melt extrusion (WO 96/14059), the limit on the content of active ingredients in pellets prepared by the aqueous extrusion methods depends critically on the degree of water-solubility of the active ingredient. Thus, for example, for active ingredients having low to poor solubility in water, pellets are known with active ingredient contents of more than 80 wt. %, the pellets still being sufficiently round and having a narrow particle size distribution despite the low content of auxiliary substances (G. A. Hileman et al., Drug Dev. Ind. Pharm., 19 (4), 483–491 (1993)). However, it is well known in the art that the higher the water-solubility of the active ingredients, the lower the quantity of active ingredient which can be incorporated into the pellets (J. M. Newton et al., Pharm. Research, 509–514 (1998); P. H. Harrison, J. Pharm. Pharmacol., 37, 686–691 (1985)). Accordingly, in the case of readily water-soluble active ingredients having a solubility in water of 0.3 g/ml, generally only pellets having an active ingredient content of at most 60 wt. % can be satisfactorily prepared by means of aqueous moist extrusion.

SUMMARY OF THE INVENTION

Accordingly, it is the object of the present invention to provide pellets containing very highly water-soluble, pharmaceutical ingredients, that is, those having a solubility in water of $\geq 0.5$ g/ml, preferably $\geq 1$ g/ml, which pellets are prepared by means of the aqueous moist extrusion process and, advantageously, have not only a defined particle size and very good roundness, but also a relatively narrow particle size spectrum.

This object is achieved by the process according to the invention for the preparation of pellets containing $\geq 50$ wt. % of a pharmaceutical active ingredient having a solubility in water of $\geq 0.5$ g/ml, by granulating the mixture containing the active ingredient with water, extruding, rounding and drying the resulting moist pellets, which is characterised in that the mixture containing the active ingredient consists of:

A) at least 50 wt. %, preferably at least 65 wt. %, of at least one active ingredient having a solubility in water of >0.5 g/ml, preferably >1 g/ml, and B) at most 50 wt. %, preferably at most 35 wt. %, of the combination of
  a) microcrystalline cellulose having an average particle size of 15 to 25 μm, determined by laser diffraction (Malvern Master Sizer) and
  b) low-substituted hydroxypropyl cellulose having an average particle size in the range of 10 to 25 μm, measured by laser diffraction, the weight ratio of a):b) being in the range of 4:6 to 6:4 and the amount of water worked into the mixture being only so much that the mixture has an adequate plasticity for extrusion and spheronization.

The term "low-substituted hydroxypropyl cellulose" is used as as defined in U.S. Pharmacopeia & National Formulary, USP 24—NF 19, page 2466 (1999) and refers to a substituted hydroxypropyl ether of cellulose which when dried at 105° for one hour contains not less than 5% nor more than 16% hydroxypropoxy groups.

The process according to the invention makes it possible to prepare pellets containing up to 90 wt. % of an active ingredient having extremely high solubility in water, that is, a solubility in water of at least 0.5 g/ml, such as, for example, tramadol hydrochloride (solubility>3.0 g/ml), chlorpromazine hydrochloride (solubility 2.5 g/ml), metamizol-Na (solubility>1 g/ml), or diphenhydramine hydrochloride (solubility 860 mg/ml).

It is essential to the process according to the invention that the auxiliary substances used, namely, microcrystalline cellulose and low-substituted hydroxypropyl cellulose, have a certain average particle size and are used in a certain weight ratio to one another. Thus one must use a microcrystalline cellulose having an average particle size of 15 to 20 μm, such as, for example, Avicel™ PH 105 or Emcocel SP 15™, or low-substituted hydroxypropyl cellulose having an average particle size in the range of 10 to 25 µm, such as, for example, 1-HPC LH 31™, 1-HPC LH 32™ or 1-HPC LH 41™, preferably having a particle size of ≦20 µm (for example, 1-HPC LH 32™, 1-HPC LH 30™ or 1-HPC LH 41™) and a hydroxypropyl content of 10 to 13 wt. % (1-HPC LH 31).

The comparison tests show that when the hitherto preferably used microcrystalline cellulose having a particle size of approximately 50 µm is used in the preparation, moist extrusion of pellets containing very readily water-soluble active ingredients such as tramadol hydrochloride, can produce only pellets with an active ingredient content of at most 40 to 45 wt. % in useful yield. Higher contents of active ingredients result in agglomeration or scarcely roundable rods of extrudate (dumb-bells) having a high dust content, depending on the quantity of water present. Surprisingly, this disadvantage can successfully be surmounted by the auxiliary substances used according to the invention.

The proportion of these auxiliary substances in the mixture containing active ingredients should be 10 to 50 wt. %, preferably from 20 to 30 wt. %, and a ratio of microcrystalline cellulose to low-substituted hydroxypropyl cellulose of 4:6 to 6:4, preferably 1:1, particularly preferably 5.1:4.9, should be maintained.

Persons skilled in the art are familiar with the remaining conditions of the process, such as the adjustment of the duration, speed and loading during the spheronization depending on the moisture content of the extrudates, the choice of the type of extruder and the spheronization conditions.

The pellets prepared by the process according to the invention initially have no controlled-release action for the incorporated highly water-soluble active ingredients. However, despite the high tendency of low-substituted hydroxypropyl cellulose to disintegrate, the pellets show no disintegration even after release of the active ingredient and residence for several hours in physiological release media. They are therefore ideal substrates to be covered with functional coatings such as, for example, coatings having controlled-release action and/or coatings which are resistant to gastric juices. It is also possible to mold the coated pellets to form rapidly disintegrating tablets, optionally in combination with uncoated pellets as an initial dose. The advantage of the formulation lies in the incorporation of high quantities of active ingredients despite their high solubility in water. Because of this, high dosages of the incorporated active ingredient can be administered in the form of small capsules or tablets, which are generally more pleasant for patients to take.

The invention accordingly also provides processes for the preparation of pellets having coatings having controlled-release action and/or which are resistant to gastric juices, optionally molded to form tablets or enclosed in capsules, by providing the pellets prepared according to the invention with appropriate coatings after preparation.

All pharmaceutically safe coating materials which are known to the person skilled in the art are suitable for use as coating materials. Preferably natural, optionally modified or synthetic polymers are used as coating materials. These are polymers such as, for example, cellulose ethers or acrylic resins. Cellulose derivatives which are insoluble in water or swellable in water are especially preferred, such as alkyl cellulose, preferably ethyl cellulose, or acrylic resins which are insoluble in water, such as poly(meth)acrylic acid and/or its derivatives, such as its salts, amides or esters. Waxes which are insoluble in water can also be used as coating materials.

These materials are known in the art, for example, Bauer, Lehmann, Osterwald, Rothgang, "Überzogene Arzneiformen", Wissenschaftliche Verlagsgesellschaft mbH, Stuttgart, 1998, page 69 ff. and are hereby incorporated by reference.

In addition to the polymers and waxes which are insoluble in water, optionally in order to adjust the release rate of the active ingredient, concomitant use may also be made of preferably up to 30 wt. % of preferably water-soluble polymers without controlled-release action, such as, for example, polyvinylpyrrolidone, or water-soluble cellulose derivatives, such as hydroxyethyl cellulose, hydroxypropyl methyl cellulose or hydroxypropyl cellulose, optionally in combination with known plasticizers.

The formulations containing active ingredients may also be provided with further coatings in addition to the controlled-release coating. In this connection, for example, a coating composed of a material which is different from the material of the controlled-release coating can be applied to the substrate surface as a separating layer without controlled-release action. Suitable covering materials for this separating layer are preferably cellulose, polyvidones, polyacrylates or even natural polymeric materials.

It is also possible to make the further coating—preferably over the coating having controlled-release action—out of the active ingredient of the substrates or out of an active ingredient which is different from these, from which this active ingredient can be released uncontrolled after oral administration. By means of this multilayered coating, after the administration of the preparation an initial dose can be made available very rapidly for the initial therapy, with the level of the active ingredient being maintained through the subsequent controlled-release administration of the active ingredient. Suitable coating materials for this are pharmaceutically safe materials in combination with the initial active ingredient such as, for example, cellulose ethers, polyvidones or polyacrylates. But it is also possible to provide yet another pharmaceutically active ingredient in the non-controlled release coating in addition to or instead of the substrate active ingredient or in addition to or instead of the aforementioned, preferably opioid, active ingredient which is different from the substrate active ingredient.

In addition, besides the coating having controlled-release action, the pellets may also have other coatings whose solubility is pH-dependent. In this way it is possible to assure, for example, that at least a portion of the pellets of a preparation pass through the gastric tract without being released, and that the active ingredients are first released in the intestinal tract.

DETAILED DESCRIPTION OF PREFERRED EMBODIMENTS

Example 1

Preparation of Tramadol Hydrochloride Pellets with an Active Ingredient Content of 55 wt. %

| | |
|---|---:|
| microcrystalline cellulose with an average particle size of 20 µm (Avicel PH 105) | 1150 g |

-continued

| | |
|---|---|
| low-substituted hydroxypropyl cellulose (1-HPC LH 31) average particle size 20 μm | 1100 g |
| Tramadol-HCl | 2750 g |

The active ingredient and the auxiliary substance were initially mixed for 10 minutes in a Diosna P25 granulator and then granulated for 10 minutes with 2100 g of purified water. The moist granular material was extruded in an extruder, model NICA E140, having a 1×2 mm die and was then rounded for 10 minutes in a spheroniser, model NICA S450, at 900 min$^{-1}$ and with a loading of 3 kg in each case. The moist pellets were dried overnight at 45° C. in a drying oven and then packaged.

The screen analysis was carried out using 100 g pellets in a vibrating screen tower from the firm Fritsch (10 min) and analytical screens having mesh sizes of 630 μm to 2000 μm. The residues on the individual screen decks were determined by weighing and the weights of the individual screen fractions were recorded as wt. % of the total sample. In each case the recorded fractions were the result of n=3 screen analyses.

| Screen fraction in μm | wt. % |
|---|---|
| <800 | 3 |
| 800–1250 | 94 |
| 1250–1400 | 3 |

The yield of round pellets having a particle size of 800 to 1250 μm was 94%.

Example 2

Preparation of Tramadol Hydrochloride Pellets with an Active Ingredient Content of 70 wt. %

| | |
|---|---|
| microcrystalline cellulose average particle size 20 μm (Avicel PH 105) | 77.5 g |
| low-substituted hydroxypropyl cellulose-average particle size 20 μm (1-HPC LH 31) | 72.5 g |
| Tramadol-HCl | 350.0 g |

The pellets were prepared in a manner similar to Example 1, except mixing of the powder and granulation were carried out with 108 g purified water in a Kenwood Chef mixer. The sample was extruded using a 1.2×2.4 mm die and spheronised; the loading of the spheroniser was approximately 600 g. The screen analysis of the pellets was performed as in Example 1.

| Screen fraction in μm | wt. % |
|---|---|
| <1000 | 1 |
| 1000–1600 | 98 |
| 1600–2000 | 1 |

The yield of round pellets having a particle size of 1000 to 1600 μm was 98%.

Example 3

Preparation of Tramadol Hydrochloride Pellets with an Active Ingredient Content of 90 wt. %

| | |
|---|---|
| microcrystalline cellulose (Emcocel SP 15) average particle size 15 μm | 27.5 g |
| low-substituted hydroxypropyl cellulose-average particle size 20 μm (1-HPC LH 31) | 22.5 g |
| Tramadol-HCl | 450.0 g |

The granulation was carried out using 70 g of purified water; otherwise the pellets were prepared and tested as in Example 2.

| Screen fraction in μm | wt. % |
|---|---|
| <1000 | 2 |
| 1000–1600 | 90 |
| 1600–2000 | 8 |

The yield of round pellets having a particle size of 1000 to 1600 μm was 90%.

Example 4

Preparation of Metamizol Sodium Pellets with an Active Ingredient Content of 80 wt. %

| | |
|---|---|
| microcrystalline cellulose (Avicel PH 105) average particle size 20 μm | 100.0 g |
| low-substituted hydroxypropyl cellulose-average particle size 10 μm (1-HPC LH 41) | 100.0 g |
| Metamizol-Na | 800.0 g |

The granulation was carried out using 200 g of purified water; a 1×2 mm die was used for the extrusion, and the loading of the spheroniser was 1200 g. Otherwise the pellets were prepared and tested as in Example 2.

| Screen fraction in μm | wt. % |
|---|---|
| <800 | 2 |
| 800–1250 | 95 |
| 1200–2000 | 3 |

The yield of round pellets having a particle size of 800 to 1250 μm was 95%.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

What is claimed is:

1. A process for preparing pellets containing ≧50 wt. % of at least one pharmaceutical active ingredient having a solubility in water of ≧1 g/ml, said process comprising the steps of:

providing a mixture consisting of:
   A) at least 50 wt. % of said at least one active ingredient, and
   B) at most 50 wt. % of a combination of:
     a. a microcrystalline cellulose having an average particle size of 15 to 20 μm, and
     b. a low-substituted hydroxypropyl cellulose having an average particle size in the range of 10 to 25 μm;
the weight ratio of a):b) being in the range of 4:6 to 6:4;
   working only so much water into the mixture that the mixture has adequate plasticity for extrusion and spheronization;
   subjecting the water-containing mixture to aqueous granulation;
   extruding the granulated mixture to pellets;
   rounding the extruded pellets, and
   drying the rounded pellets.

2. A process according to claim 1, wherein the active ingredient is tramadol hydrochloride having a solubility in water of >3.0 g/ml, or metamizol-Na having a solubility in water of 1 g/ml, or diphenhydramine hydrochloride having a solubility in water of 1 g/ml.

3. A process according to claim 1, wherein the weight ratio a):b) is 1:1.

4. A process according to claim 3, wherein the active ingredient is tramadol hydrochloride having a solubility in water of >3.0 g/ml, or metamizol-Na having a solubility in water of 1 g/ml, or diphenhydramine hydrochloride having a solubility in water of 1 g/ml.

5. A process according to claim 1, wherein the pellets have an active ingredient content from greater than 50 wt. % up to 90 wt. %.

6. A process according to claim 1, further comprising the step of coating the pellets with a coating having a controlled-release action.

7. A process according to claim 1, further comprising the step of coating the pellets with a coating which is resistant to gastric juices.

8. A process according to claim 1, further comprising coating the pellets with a coating having a controlled-release action, and coating the pellets with a coating which is resistant to gastric juices.

9. A process according to claim 1, further comprising enclosing the pellets in capsules.

10. A process according to claim 1, further comprising molding the pellets into tablets.

11. A process according to claim 1, wherein the mixture contains at least 65 wt. % of component A) and at most 35 wt. % of the combination B).

* * * * *